(12) United States Patent
Sharpless et al.

(10) Patent No.: US 8,681,930 B2
(45) Date of Patent: Mar. 25, 2014

(54) HIGH SPEED ROTATING GANTRY

(75) Inventors: Ronald B. Sharpless, Cleveland, OH (US); Rosemarie Sheridan, Mayfield Village, OH (US); John P. Cressman, Chardon, OH (US)

(73) Assignee: Koninklijke Philips N.V., Eindhoven (NL)

( * ) Notice: Subject to any disclaimer, the term of this patent is extended or adjusted under 35 U.S.C. 154(b) by 623 days.

(21) Appl. No.: 12/742,131

(22) PCT Filed: Nov. 4, 2008

(86) PCT No.: PCT/IB2008/054590
§ 371 (c)(1),
(2), (4) Date: May 10, 2010

(87) PCT Pub. No.: WO2009/063354
PCT Pub. Date: May 22, 2009

(65) Prior Publication Data
US 2010/0266105 A1 Oct. 21, 2010

Related U.S. Application Data

(60) Provisional application No. 60/988,443, filed on Nov. 16, 2007.

(51) Int. Cl.
*A61B 6/03* (2006.01)
(52) U.S. Cl.
USPC .............................................. 378/4; 378/197
(58) Field of Classification Search
CPC ............................... A61B 6/035; A61B 6/4435
USPC .................................. 378/4, 197, 15, 196, 198
See application file for complete search history.

(56) References Cited

U.S. PATENT DOCUMENTS

| | | | |
|---|---|---|---|
| 5,703,921 A * | 12/1997 | Fujita et al. | 378/4 |
| 5,761,269 A | 6/1998 | Sugihara et al. | |
| 6,276,145 B1 | 8/2001 | Sharpless et al. | |
| 2004/0062356 A1* | 4/2004 | Brunnett | 378/196 |
| 2004/0081270 A1* | 4/2004 | Heuscher | 378/4 |
| 2004/0120451 A1* | 6/2004 | Tsukagoshi et al. | 378/4 |
| 2004/0161074 A1 | 8/2004 | Kresse | |
| 2005/0013403 A1* | 1/2005 | Reznicek et al. | 378/15 |

FOREIGN PATENT DOCUMENTS

DE 102006045396 A1 4/2008
EP 1762177 A2 3/2007

* cited by examiner

Primary Examiner — Glen Kao

(57) ABSTRACT

A medical imaging apparatus includes a stationary gantry and a generally spool-shaped rotating gantry (304), which rotates about an examination region about a longitudinal axis. The rotating gantry includes a first flange (320), a second flange (322), and a plurality of elongate structural elements (402) that are disposed between and couple' the first and second flanges. The first flange (320) is rotatably coupled to the stationary gantry, and the second flange (322) extends radially in a plane perpendicular to the longitudinal axis, thereby providing radial stiffness for the rotating gantry. A radiation source is affixed to the rotating gantry between the first and second flanges, and a detector array is affixed to the rotating gantry between the first and second flanges, opposite the examination region from the radiation source.

23 Claims, 4 Drawing Sheets

(A) (B) (C)

(A) (B) (C)

HIGH SPEED ROTATING GANTRY

CROSS REFERENCE TO RELATED APPLICATIONS

This application claims the benefit of U.S. provisional application Ser. No. 60/988,443 filed Nov. 16, 2007, which is incorporated herein by reference.

The present application relates to a medical imaging system, and finds particular application to computed tomography (CT). It also amenable to other medical imaging applications and to non-medical imaging applications.

Generally, computed tomography (CT) scanners used for medical imaging applications include a stationary gantry/frame assembly and a rotating gantry/frame assembly, which rotates with respect to the stationary gantry about an examination region along a longitudinal or z-axis. The rotating gantry is supported on the stationary gantry via a bearing.

A radiation source and other components, such as a heat exchanger, a collimator, a power module and/or other components, are affixed to the rotating gantry and rotate about the examination region when the rotating gantry rotates about the examination region. In a third generation system, an array of radiation sensitive detectors is also affixed to the rotating gantry and is located opposite the radiation source with respect to the examination region. With a fourth generation system, the array of the radiation sensitive detectors is affixed to the stationary gantry.

In one configuration, the rotating gantry is based on a single plate rotor topology in which the radiation source and the detector array (third generation system) are affixed to a plate-shaped rotor such that the radiation source and the detector array cantilever from the plate-shaped rotor. An example of such a configuration is shown in FIGS. 1A, 1B, and 1C. In these figures, a radiation source 102 and a detector array 104 cantilever from a side of a plate-shaped rotor 106, and the radiation source 102 produces a radiation beam 108 that traverse an examination region 110 and illuminates the detector array 104.

Unfortunately, the single plate-shaped rotor 106 may physically distort in a direction along the z-axis, as shown in FIG. 1C, due to radial g-forces associated with the components supported on the plate-shaped rotor 106 when the single plate-shaped rotor 106 rotates. Generally, the physical distortion increases with rotor rotation speed such that the distortion is relatively greater, for example, at a rotor rotation speed of 180 revolutions per minute (RPM) as compared to a rotor rotation speed of 60 RPM. A consequence of such a distortion is that the radiation beam 108 drifts along the detector array 104. FIG. 1C shows an exaggerated drift.

With some lower rotor rotation speed (e.g., 60 RPM scanners) single and dual slice scanners, a width of the detectors in the detector array 104 along the z-axis is increased so that the radiation beam 108 illuminates the detector array 104 over a range of radiation beam drift. However, such an increase in detector width may lead to increased detector cost. Alternatively, a width of the radiation beam 108 along the z-axis may be increased so that the radiation beam 108 illuminates the detector array 104 over a range of radiation beam drift. However, widening the radiation beam may lead to decreased radiation efficiency, or increased patient/object dose. With some scanners, increasing the detector width and/or increasing the beam width may not be desirable.

In another configuration, the rotating gantry is based on a cylinder rotor topology in which the radiation source and the detector array (third generation system) are affixed to a cylindrically-shaped rotor. An example of such a configuration is shown in FIGS. 2A, 2B, and 2C. In these figures, a radiation source 202 and a detector array 204 are affixed to opposing sides of a cylindrically-shaped rotor 206, and the radiation source 202 produces a radiation beam 208 that traverse an examination region 210 and illuminates the detector array 204.

Unfortunately, the cylindrically-shaped rotor 206 may physically distort along a radial direction, as shown in FIG. 2C, due to radial g-forces associated with the components supported on the plate-shaped rotor 206 when the cylindrically-shaped rotor 202 rotates. As with the plate-shaped rotor topology, the corresponding distortion generally increases with rotor rotation speed such that the distortion is greater at higher rotor rotation speeds. Since reconstruction is dependant upon a substantially constant physical relationship between the radiation source 202 and the detector array 204, such physical distortion or other geometrical distortion may introduce artifact that is propagated to the volumetric image data and images generated therefrom.

The single plate and the cylinder rotor topologies have been combined to provide incremental improvements over each of the single rotor plate and the rotor cylinder topologies with respect to the above-noted physical rotor distortions.

However, continuing advances in scanner related technology are leading to scanners that are capable of rotating at much higher speeds, for example, over 200 RPM. As the rotor rotation speed increases, the rotor is exposed to a greater g-force, for example, a g-force of 30 g or greater in the radial direction. As a consequence, the above-noted physical rotor distortions are exaggerated and more prominent.

Aspects of the present application address the above-referenced matters and others.

According to one aspect, a medical imaging apparatus includes a stationary gantry and a generally spool-shaped rotating gantry, which rotates about an examination region about a longitudinal axis. The rotating gantry includes a first flange, a second flange, and a plurality of elongate structural elements that are disposed between and couple the first and second flanges. The first flange is rotatably coupled to the stationary gantry, and the second flange extends radially in a plane perpendicular to the longitudinal axis, thereby providing radial stiffness for the rotating gantry. A radiation source is affixed to the rotating gantry between the first and second flanges, and a radiation sensitive detector is affixed to the rotating gantry between the first and second flanges, opposite the examination region from the radiation source.

According to another aspect, a rotating gantry includes a first flange configured for rotatably coupling to a stationary gantry. The rotating gantry further includes a second flange that provides radial stiffness for the rotating gantry when the rotating gantry rotates. A plurality of elongate structural elements are disposed between and couple the first and second flanges.

According to another aspect, a method includes rotating a spool-shaped rotating gantry about an examination region. The spool-shaped rotating gantry includes a radiation source and a detector array. The method further includes generating a radiation beam with the radiation source, detecting radiation emitted by the radiation source with the detector array, and generating volumetric image data from a signal indicative of the detected radiation.

The invention may take form in various components and arrangements of components, and in various steps and arrangements of steps. The drawings are only for purposes of illustrating the preferred embodiments and are not to be construed as limiting the invention.

FIGS. 1A, 1B, and 1C illustrate a prior art single plate-shaped rotor topology.

FIGS. 2A, 2B, and 2C illustrate a prior art cylinder-shaped rotor topology.

Figure 1:
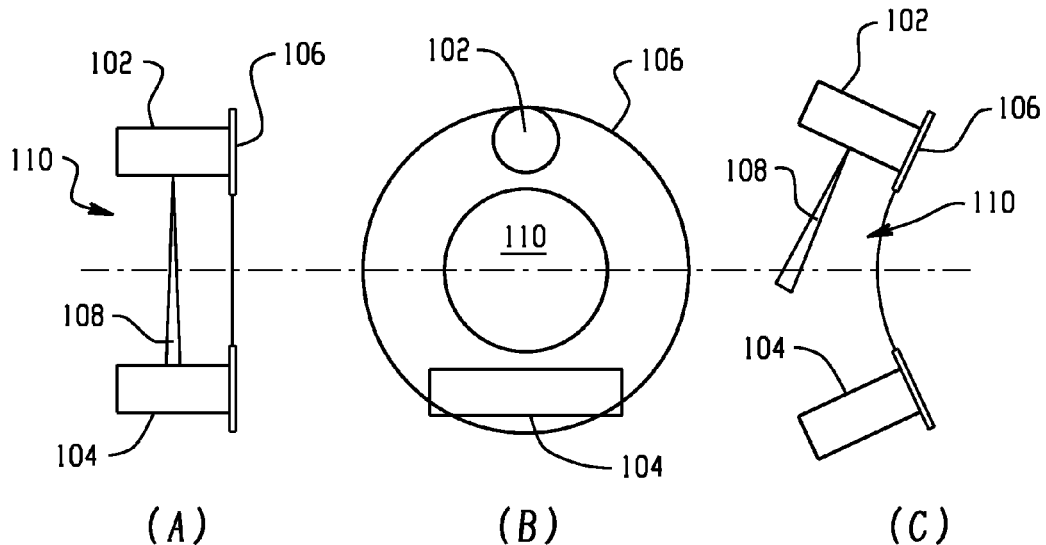
Figure 2:
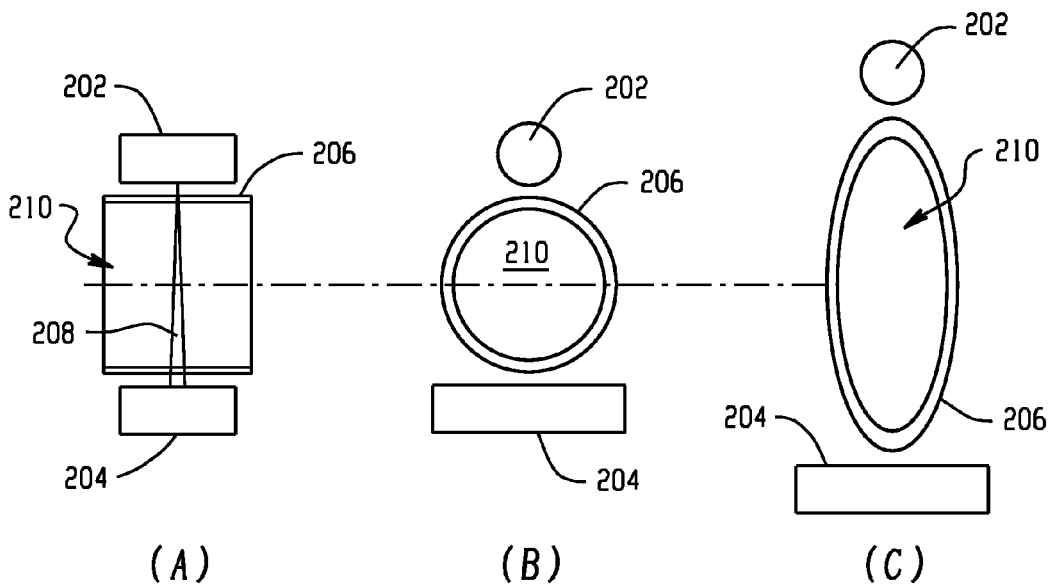
Figure 3:
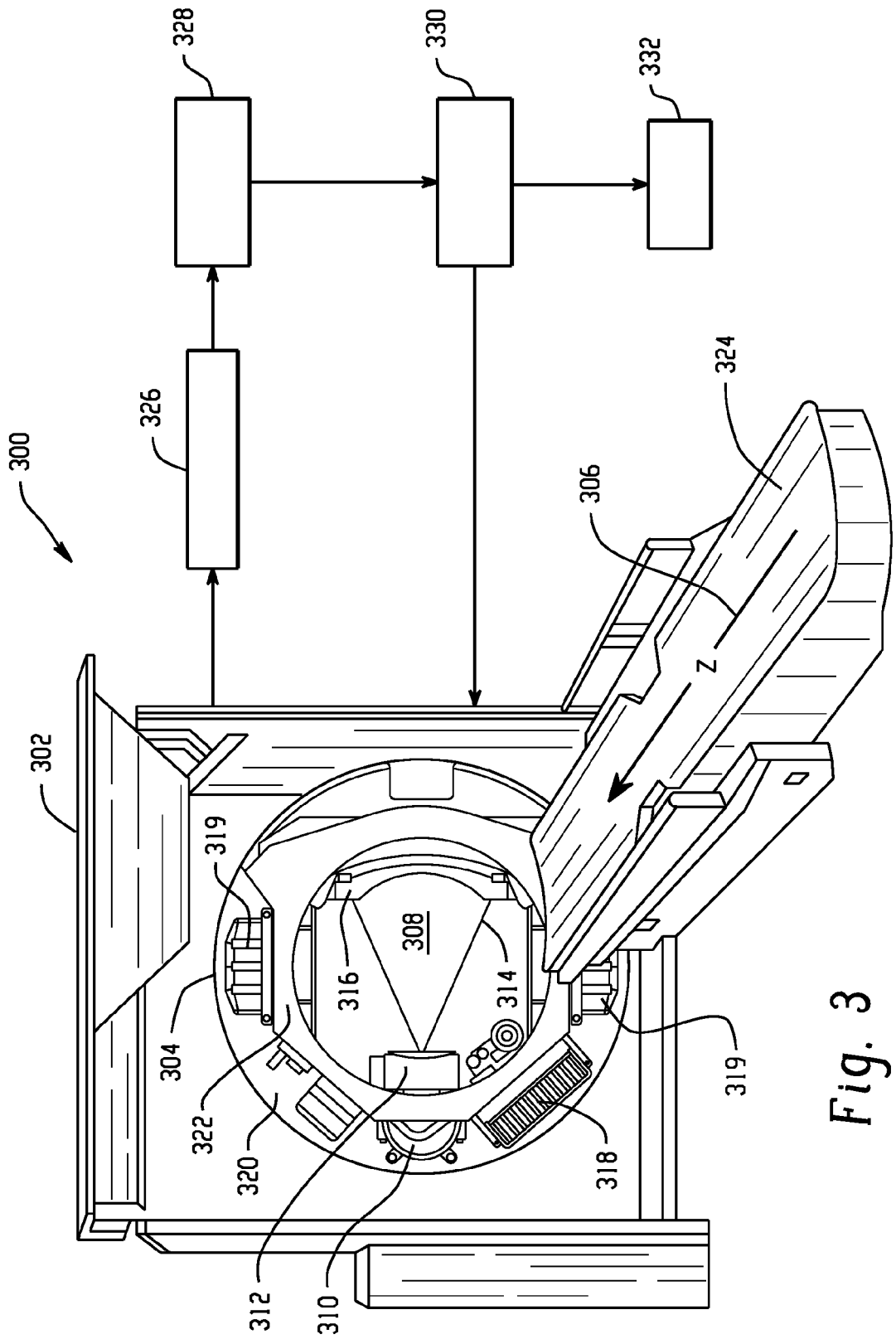
FIG. 3 illustrates an example CT scanner.

Initially with reference to FIG. 3, a computed tomography (CT) scanner 300 includes a stationary gantry 302 and a rotating gantry 304. The stationary gantry 302 is stationary in that it is generally stationary during a scan. However, it may be configured to tilt or otherwise be moved.

The rotating gantry 304 is supported on the stationary gantry 302 via a bearing (not visible). Non-limiting examples of suitable bearings include a mechanical bearing, such as one with rolling balls interposed between two raceways, a fluid bearing, such as an air bearing that provides an air barrier between the rotating gantry 304 and the stationary gantry 302, and other bearings. An example of a suitable fluid bearing is described in patent application Ser. No. 09/428, 431, filed Oct. 27, 1999, and entitled "Aerostatic CT suspension."

The rotating gantry 304 rotates about a z-axis 306 around an examination region 308. In the illustrated example, the rotating gantry 304 is configured to rotate at rotation speeds greater than 200 revolutions per minute (RPM) such as 220 RPM or more. The rotating gantry 304 is also configured to rotate at lower rotation speeds.

The rotating gantry 304 supports a radiation source 310, such as an x-ray tube that emits radiation. The rotating gantry 304 also supports a source collimator 312 that collimates the radiation emitted by the radiation source 310 to produce a generally conical or fan shaped radiation beam 314. As shown, the radiation beam 314 traverses the examination region 308.

With the illustrated third generation CT scanner 300, the rotating gantry 304 also supports a radiation sensitive detector array 316 that subtends an angular arc on a side of the examination region 308 opposite the radiation source 310. A fourth generation CT configuration is also contemplated. The illustrated detector array 316 includes multiple rows of radiation sensitive detector elements that extend in the z-axis direction, and multiple columns of radiation sensitive detector elements that extend in a traverse direction. A single row detector array is also contemplated. The detector elements detect radiation that traverses the examination region 308.

The rotating gantry 304 also supports a heat exchanger 318, a power module 319, and/or various other components such as one or more patient positioning lasers, a rotor angular position measurement device, a data transfer module, cabling, balancing weights, and/or other components.

In the illustrated embodiment, the rotating gantry 304 includes a spool-shaped rotor that it includes flanges 320 and 322 coupled together by elongate structural elements 402 (FIG. 4) disposed therebetween. As described in greater detail below, in one instance the flanges 320 and 322 include a dimension such as shape and a size configured to provide radial stiffness and the elongate structural elements 402 include a dimension and location configured to provide axial stiffness. As a result, in one instance the rotating gantry 304 may be less prone to physical distortions due to radial g-forces when the rotating gantry 304 rotates at relatively high rotation speeds, such as rotation speeds greater then 200 RPM, relative to an embodiment in which the flanges 320 and 322 and the elongate structural elements 402 are otherwise configured.

A patient support 324, such as a couch, supports a patient in the examination region 308. The patient support 324 is movable along the z-axis 306 in coordination with the rotation of the rotating gantry 304 to facilitate helical, axial, or other desired scanning trajectories.

A reconstructor 326 reconstructs projection data from the detectors to generate volumetric data indicative of the interior anatomy of the patient. An image processor 328 processes the volumetric image data generated by the reconstructor 326 for display in human readable form.

A general purpose computing system serves as an operator console 330. The operator console 330 includes human readable output devices such as a display 332 and/or printer and input devices such as a keyboard and/or mouse. Software resident on the console 330 allows the operator to control the operation of the system 300, for example, by allowing the operator to select a scan protocol, initiate scanning, terminate scanning, view and/or manipulate the volumetric image data, and/or otherwise interact with the system 300.

The rotating gantry 304 is now described in further detail in connection with FIGS. 4 and 5. Initially referring to FIG. 4, a perspective view of the rotating gantry 304, without the components supported thereby, is illustrated. As briefly discussed above, the rotating gantry 304 includes the first and second flanges 320 and 322 coupled together by the elongate structural elements 402.

The first flange 320 includes first and second major surface 404 and 406, both extending generally perpendicular to the longitudinal axis 306 (FIG. 3). The first major surface 404 is operatively coupled to the bearing (not visible). The second major surface 406 is operatively coupled to the elongated structural elements 402. The second flange 322 includes first and second major surface 408 and 410, both extending generally perpendicular to the longitudinal axis 306. The first major surface 408 faces away from the elongate structural elements 402, and the second major surface 410 is operatively coupled to the elongate structural elements 402. As shown, in this example the first and second flanges 320 and 322 are positioned generally parallel to each other, with their respective second surfaces 406 and 410 facing each other.

The dimensions of the second flange 322, in a plane perpendicular to the longitudinal axis 306, is application dependent. In the illustrated example, the second flange 402 includes a shape and size that is determined based on the operable rotor rotation speeds, the mass of the components supported on the rotating gantry 304, a level of acceptable radial distortion, and component accessibility. By way of example, for a particular level of distortion and known mass, the shape and size may correspond to a shape and size that provides suitable radial stiffness at a maximum or other rotor rotation speed so that the radial distortion of the rotating gantry 304, if any, does not exceed the particular level of distortion. The particular level of distortion may be based on image quality, the ability to correct for distortion (via hardware and/or software techniques), and/or other considerations. In general, the larger the flange is in the plane perpendicular to the longitudinal axis 306, the greater the radial stiffness. However, the shape and size is also determined in a manner to reduce or minimize the need to remove the second flange 322 or maximize access to the components when accessing the components supported on the rotating gantry 304. The illustrated shape and size is one non-limiting example of a suitable shape and size for the illustrated CT scanner 300. It is to be appreciated that the second flange 322 and the first flange 320 may be substantially equal in size.

Other factors may alternatively or additionally be considered when determining the shape and size of the second flange 322.

Figure 4:
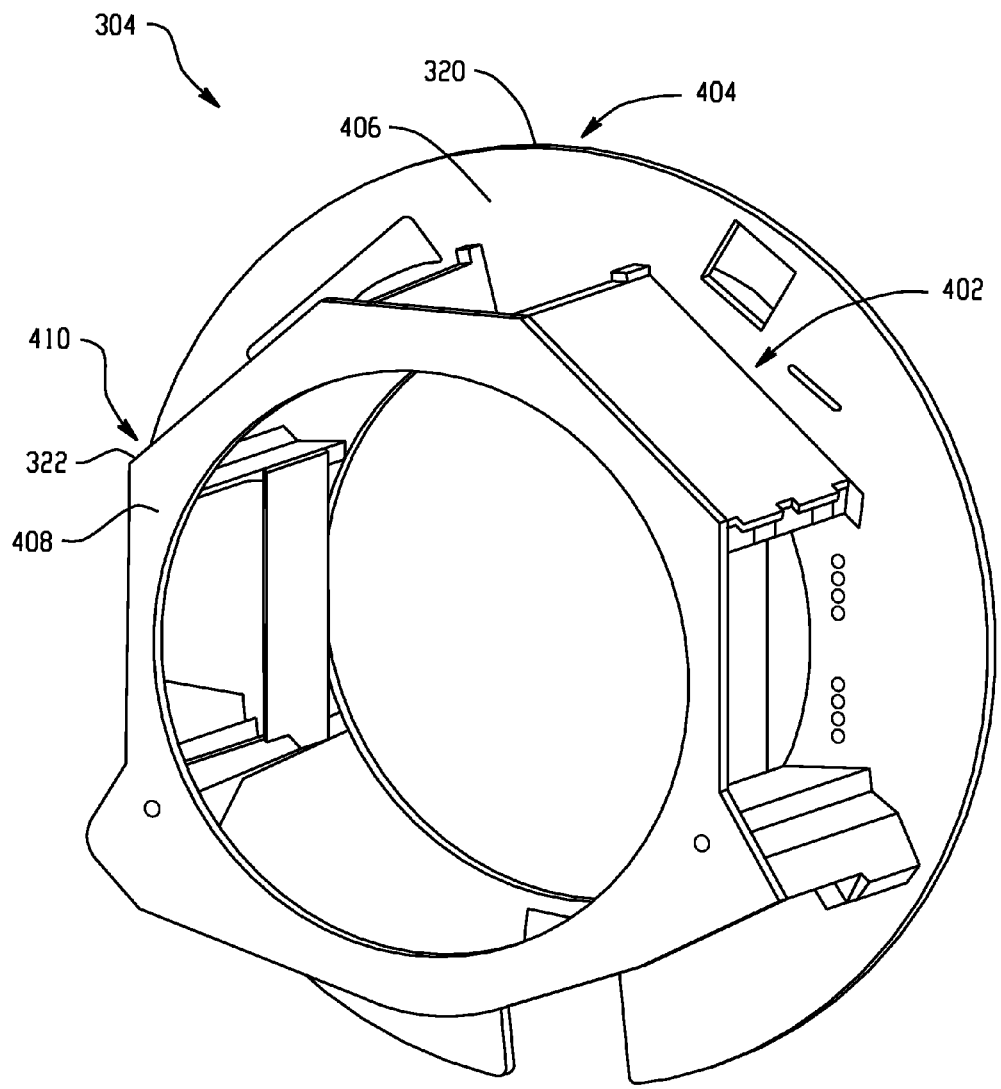
FIG. 4 illustrates an example rotating gantry.
Figure 5:
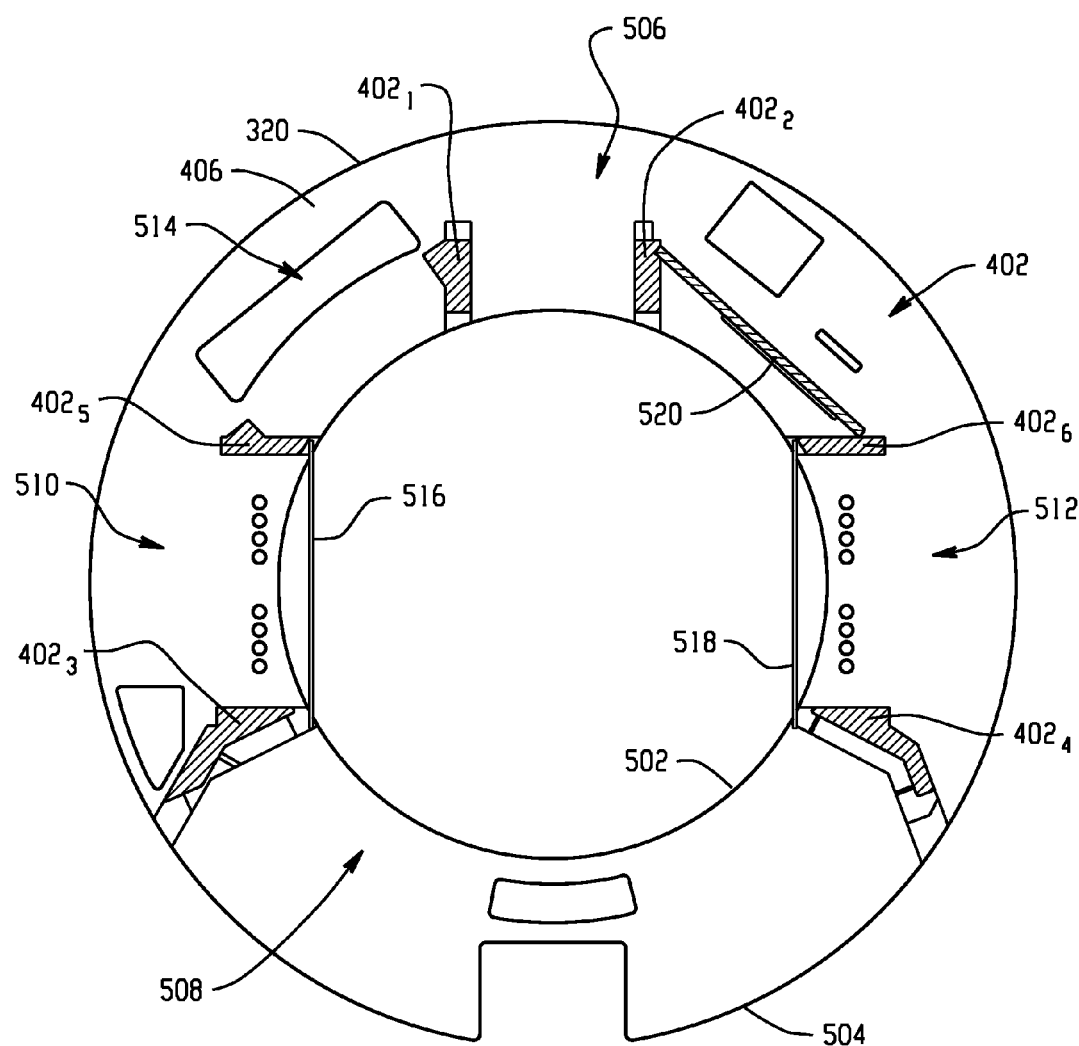
FIG. 5 illustrates an example rotating gantry with various other components attached thereto.

Turning to FIG. 5, a sectional view of FIG. 4 is illustrated. The dimensions and locations of the elongate structural elements 402 are determined based on a location of the supported components, the rotor rotation speeds, the mass of the supported components, and a level of acceptable axial distortion.

By way of example, structural elements $402_1$ and $402_2$ are positioned on the first flange 320 in manner that leaves a first opening 506 therebetween dimensioned so that at least a first portion of the radiation source 310 (FIG. 3) is disposed between the structural elements $402_1$ and $402_2$ when the radiation source 310 is installed on the rotating gantry 304. The structural elements $402_1$ and $402_2$ extend perpendicularly from the first flange 404, extend radially in a plane parallel to the longitudinal axis, and have a non-zero finite width. In this example, the height of the structural elements $402_1$ and $402_2$ extends a sub-portion of a distance between an inner perimeter 502 and an outer perimeter 504 of the first flange 320, and the structural elements $402_1$ and $402_2$ are positioned nearer to the inner perimeter 502 with respect to the outer perimeter 504. Such dimensions and locations of the structural elements $402_1$ and $402_2$ can provide substantial symmetrical structural stiffness about the installed radiation source 310, for example, for the particular rotation speed, known mass, and particular acceptable level of rotor physical distortion. The illustrated dimensions and locations of the structural elements $402_1$ and $402_2$ is one non-limiting example of suitable dimensions and locations for the illustrated CT scanner 300.

Structural element $402_3$ and $402_4$ are positioned on the first flange 320 in manner that leaves a second opening 508, in which at least a sub-portion of the detector array 316 (FIG. 3) fits between when the detector array 316 is installed on the rotating gantry 304. Likewise, the structural element $402_3$ and $402_4$ extend perpendicularly from the first flange 320 and have a non-zero, finite width and height in a plane parallel to the longitudinal axis. As shown, the height of the structural elements $402_3$ and $402_4$ extend along a sub-portion of a distance between the inner and outer perimeters 502 and 504, and are located nearer to the inner perimeter 502. Such dimensions and locations of the structural elements $402_3$ and $402_4$ can provide substantial symmetrical structural stiffness about the installed detector array 316, for example, for the particular rotation speed, known mass, and the particular level of rotor physical distortion. The illustrated dimensions and locations of the structural elements pairs $402_3/402_4$ and $402_5/402_6$ is one non-limiting example of suitable dimensions and locations for the illustrated CT scanner 300.

The structural element pairs $402_3/402_5$ and $402_4/402_6$ define third and fourth opening 510 and 512 for installation of the power modules 319 (FIG. 3), and the structural element pairs $402_1/402_5$ define a fifth opening 514 for installation of the heat exchanger 318 (FIG. 3). The dimensions and locations of the structural elements pairs $402_3/402_5$, $402_4/402_6$, and $402_1/402_5$ provide structural stiffness about the installed power modules 319 and installed heat exchanger 318.

In FIG. 5, connecting supports 516, 518, and 520 are employed. In particular, the connecting support 516 is disposed between and couples the structural elements $402_3$ and $402_5$, the connecting support 518 is disposed between and couples the structural elements $402_4$ and $402_6$, and the connecting support 520 is disposed between and couples the structural elements $402_2$ and $402_6$. As can be seen, in one instance the connecting supports are employed between structural elements where such a connecting support would not interfere with a component supported on the rotating gantry 304. Such supports 516, 518, and 520 may provide further axial stiffness. The supports 516, 518, and 520 may also provide shear stiffness. As such, the major surfaces 406 and 408 remain concentric. The connecting supports 516, 518, and 520 may also be omitted.

It is noted that the components installed on the rotating gantry 304, for example, the radiation source 310, the collimator 312, the detector array 316, the heat exchanger 318, and the power module 319, may also provide further structural stiffness for the rotating gantry 304.

In the illustrated configuration, when the radiation source 310, the detector array 316, and the heat exchanger 318 are installed on the rotating gantry 304, the combination of the structural elements 402, the connecting supports 516, 518, and 520, and the installed components aggregately form a generally cylindrical section between the first and second flanges 320 and 322.

With respect to FIGS. 3, 4 and 5, in the illustrated embodiment the first and second flanges 320 and 322 are formed from steel or the like, and the structural elements 402 are formed from aluminum or the like. The first and second flanges 320 and 322 are both fastened to the structural elements 402. In one instance, the first and second flanges 320 and 322 and the structural elements 402 are fastened together via bolts, rivets or the like, and then the various components are affixed to the rotating gantry 304. In another instance, the first flange 320 and the structural elements 402 are fastened together, the various components are affixed to the rotating gantry 304, and then the second flange 322 and the structural elements 402 are fastened together. Other approaches for affixing the components to the rotating gantry 304 (the flanges 320 and 322, and the structural elements 402) and the components supported on the rotating gantry 304 are also contemplated.

Variations are contemplated.

As noted above, the illustrated first and second flanges 320 and 322 are formed from steel and the structural elements 402 are formed from aluminum. In another embodiment, the rotating gantry 304, including the first and second flanges 320 and 322 and the structural elements 402, is formed as a single unitary structure via an aluminum or other casting. In yet another embodiment, the first and second flanges 320 and 322 are substantially permanently mounted to the structural elements 402, for example, via welding.

In the embodiment illustrated in the figures, the second flange 322 is a single unitary structure that is fastened with the structural elements 402. In another embodiment, the second flange 322 includes two or more separate sub-sections that individually fasten to different pairs of the structural elements 402. In yet another embodiment, the two or more separate sub-sections are affixed to different components, and affixing the components to the rotating gantry 304 affixes the second flange 322 to the rotating gantry 304.

As shown in FIG. 5, the structural elements 402 are disposed nearer an inner perimeter 502 of the first flange 320. However, in another embodiment, the structural elements 402 are disposed nearer an outer perimeter 504. With this configuration, the connecting supports 516-520 may also be affixed to end regions of the structural elements that nearer to the outer perimeter 504. In yet another embodiment, the structural elements 402 are approximately centered between the inner and outer perimeters 502 and 504. In yet another embodiment, the structural elements 402 substantially extend the distance between the inner and outer perimeters 502 and 504. In such an instance, connecting supports similar to the connecting supports 516-520 may alternatively or additionally be coupled to the end regions of the structural elements that are nearer to the outer perimeter 504.

It is also to be appreciated that the rotating gantry 304 can be used in connection with other imaging systems, for example, positron emission and single photon emission tomography, in which it is desirable to rotate one or more components.

It is also to be appreciated that the stiffness of the rotating gantry 304 may also facilitate reducing radiation exposure, reducing imaging system calibration, mitigating active pre-examination region collimation, mitigating active post-examination region collimation.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. A medical imaging apparatus, comprising:
    a stationary gantry;
    a generally spool-shaped rotating gantry, which rotates about an examination region about a longitudinal axis, the rotating gantry including:
        a first flange that is rotatably coupled to the stationary gantry;
        a second flange that extends radially in a plane perpendicular to the longitudinal axis, thereby providing radial stiffness for the rotating gantry; and
        a plurality of elongate structural support elements that are disposed between and couple the first and second flanges; and
    a data acquisition system mounted to the generally spool-shaped rotating gantry, wherein the plurality of elongate structural support elements are not part of the data acquisition system, the data acquisition system at least comprising:
        an x-ray radiation source affixed to the rotating gantry between the first and second flanges; and
        a detector array affixed to the rotating gantry between the first and second flanges, opposite the examination region from the x-ray radiation source.

2. The medical imaging apparatus of claim 1, wherein the rotating gantry rotates at speeds greater than two hundred revolutions per minute.

3. The medical imaging apparatus of claim 1, wherein a first pair of the elongate structural support elements are positioned on the first flange, leaving a first opening there between dimensioned so that at least a first portion of the radiation source is disposed between the pair of the elongate structural support elements, wherein none of the elongate structural support elements are in the opening.

4. The medical imaging apparatus of claim 1, wherein the data acquisition system further includes at least a heat exchanger and a power module.

5. The medical imaging apparatus of claim 1, wherein the second flange includes a plurality of sub-sections that are removeably fastened together.

6. The medical imaging apparatus of claim 5, wherein a first sub-section of the plurality of sub-sections removeably fastens to the x-ray radiation source, and a second sub-section of the plurality of sub-sections removeably fastens to the detector array.

7. The medical imaging apparatus of claim 1, wherein the first and second flanges are substantially the same size.

8. The medical imaging apparatus of claim 1, wherein the first flange includes an inner perimeter and an outer perimeter, and the plurality of elongate structural elements radially extend from about the inner perimeter toward the outer perimeter.

9. The medical imaging apparatus of claim 1, wherein the plurality of elongate structural elements provide axial stiffness for the rotating gentry.

10. The medical imaging apparatus of claim 1, wherein at least one pair of the plurality of elongate structural elements radially extends along sides of the radiation source.

11. The medical imaging apparatus of claim 10, wherein the plurality of elongate structural elements provide symmetrical axial support about the x-ray radiation source.

12. The medical imaging apparatus of claim 1, wherein the first and second flanges are formed from steel, and the plurality of elongate structural elements are formed from aluminum.

13. The medical imaging apparatus of claim 1, further including an air bearing, wherein the air bearing operatively couples the first flange to the stationary gantry.

14. A rotating gantry, comprising:
    a first flange configured for rotatably coupling to a stationary gantry;
    a second flange that provides radial stiffness for the rotating gantry when the rotating gantry rotates; and
    a plurality of elongate structural elements that are disposed between and that couple the first and second flanges, forming a spool shaped rotating gantry, wherein the plurality of elongate structural support elements are not part of a data acquisition system, the data acquisition system at least comprising an x-ray radiation source and a detector array.

15. The rotating gantry of claim 14, wherein the rotating gantry rotates at speeds greater than two hundred revolutions per minute.

16. The rotating gantry of claim 14, further including at least one of an x-ray radiation source, a detector array, a heat exchanger, and a power module, wherein the at least one of the x-ray radiation source, the detector array, the heat exchanger, and the power module is affixed between the first and the second flanges.

17. The rotating gantry of claim 16, wherein the second flange includes a shape that allows a human to access at least one the x-ray radiation source, the detector array, the heat exchanger, and the power module.

18. The rotating gantry of claim 16, wherein the second flange includes a plurality of different sub-sections, wherein at least one of the sub-sections is coupled to one of the x-ray radiation source, the detector array, the heat exchanger, and the power module.

19. The rotating gantry of claim 16, wherein at least one of the plurality of elongate structural elements radially extends along sides of one of the x-ray radiation source, the detector array, the heat exchanger, and the power module.

20. The rotating gantry of claim 14, wherein the second flange includes a plurality of different sub-sections that are individually coupled to the plurality of elongate structural elements.

21. The rotating gantry of claim 14, wherein the plurality of elongate structural elements provide axial stiffness for the rotating gantry.

22. The rotating gantry of claim 14, wherein the rotating gantry is part of a computed tomography system.

23. A method, comprising:
    rotating a spool-shaped rotating gantry about an examination region, wherein the spool-shaped rotating gantry includes an x-ray radiation source and a detector array, the spool-shaped rotating gantry including:
  a first flange;
  a second flange; and
  a plurality of elongate structural support elements disposed between, coupling the first and second flanges, wherein the plurality of elongate structural support elements are not part of the x-ray radiation source and the detector array;
generating an x-ray radiation beam with the x-ray radiation source;
detecting x-ray radiation emitted by the x-ray radiation source with the detector array; and
  generating volumetric image data from a signal indicative of the detected x-ray radiation.

\* \* \* \* \*